United States Patent [19]

Fossel et al.

[11] 4,413,233

[45] Nov. 1, 1983

[54] DYNAMIC NMR MEASUREMENT

[75] Inventors: Eric T. Fossel; Joanne S. Ingwall, both of W. Newton, Mass.

[73] Assignee: President and Fellows of Harvard College, Cambridge, Mass.

[21] Appl. No.: 279,721

[22] Filed: Jul. 2, 1981

[51] Int. Cl.³ .......................................... G01R 33/08
[52] U.S. Cl. ..................................... 324/300; 324/309
[58] Field of Search ............... 324/300, 306, 309, 316; 128/709

[56] References Cited

U.S. PATENT DOCUMENTS 3,911,905 10/1975 Rossel .................................. 128/709

OTHER PUBLICATIONS

Jacobus et al. (1977), Nature 265, 756.
Mansfield, "Short Communications Human Whole Body Line-Scan Imaging by NMR", British Journal of Radiology, 51, No. 611, Nov. 1978, pp. 921-922.
Hutchison, "Electron Spin Resonance Spectrometry on the Whole Mouse in Vivo: a 100 MHz Spectrometer", J Physe E (G.B.), vol. 4, No. 3, Mar. 1971, pp. 237-239.

Primary Examiner—Michael J. Tokar

[57] ABSTRACT

Apparatus and method for dynamically measuring a chemical entity in living biological tissue having a physical characteristic capable of fluctuation, the apparatus including an NMR pulse spectrometer capable of providing an observation pulse for instantaneously measuring the spectrum of the chemical entity in the tissue, sensing means for sensing the physical characteristic and providing an output signal, and triggering means responsive to the sensing means output signal and connected to the spectrometer for triggering the spectrometer to produce the observation pulse at a selected point in the course of the fluctuation of the physical characteristic of the tissue.

10 Claims, 8 Drawing Figures

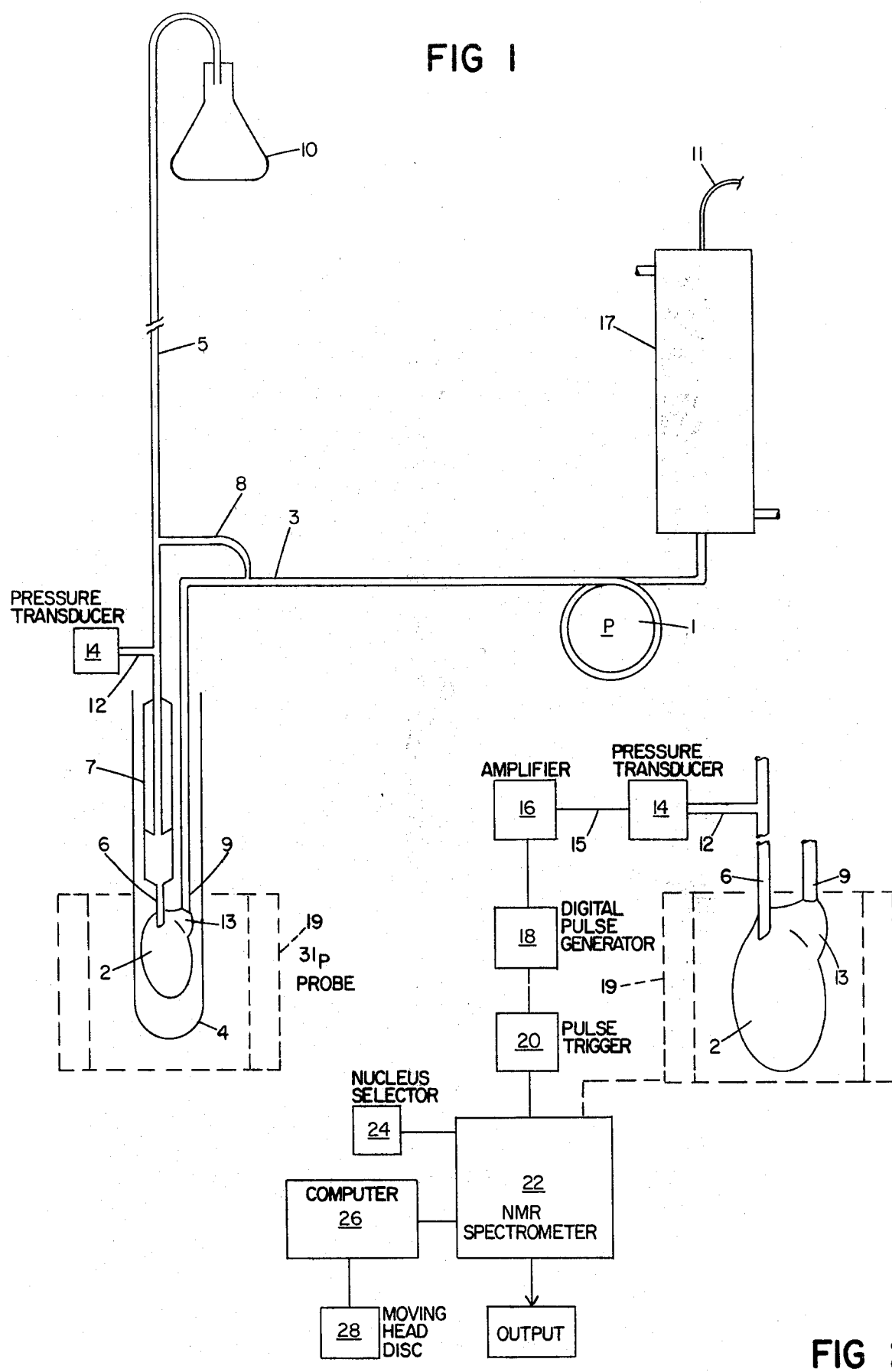

DYNAMIC NMR MEASUREMENT

This invention relates to the use of nuclear magnetic resonance (NMR) spectroscopy to measure chemical entities in biological tissues.

NMR spectroscopy has been used for many years to provide information about the structure of organic compounds. The technique is based on the theory that the nuclei of hydrogen atoms possess magnetic moments when placed in a magnetic field, and that these moments can be aligned either with, or against, that field. Electromagnetic energy passed through the compound can, if at a proper frequency, be absorbed, changing the magnetic moment alignment of some of the nuclei. The frequency at which absorbance occurs for the nuclear spins of any element existing in different environments within a compound provides information about the structure and environment of the compound containing the atomic nucleus under observation.

More recently, phosphorous-31 ($^{31}P$) NMR has been used to follow the metabolism of phosphate-containing molecules such as ATP and creatin phosphate (CrP) in intact, living tissues such as skeletal muscle and isolated, perfused hearts. However, none of the studies employing living systems has successfully measured changes in levels of chemical entities in dynamic or oscillating systems. Such information would, however, be of great importance. For example, changes in ATP and CrP levels are believed to occur during the cardiac cycle. The nature of such changes may reflect the mechanism by which the heart regulates its internal energy supply and demand requirements. Particular deviations from the normal cycle may be specific for particular disease states. Other dynamic biological tissues undoubtedly metabolize chemical entities cyclically as well.

The present invention provides a method and apparatus for dynamically measuring a chemical entity in living biological tissue (used herein to include either a piece of excised tissue, an organ, or an entire animal) having a physical characteristic capable of fluctuation.

The apparatus includes an NMR pulse spectrometer capable of providing an observation pulse for instantaneously measuring the spectrum of the chemical entity in the tissue, sensing means for sensing the physical characteristic and providing an output signal, and triggering means responsive to the sensing means output signal and connected to the spectrometer for triggering the spectrometer to produce the observation pulse at a selected point in the course of the fluctuation of the physical characteristic of the tissue, apparatus for measuring a chemical entity in living tissue having a cyclical physical characteristic is as described above, with the triggering means being capable of triggering the spectrometer to produce the observation pulse at a selected point in the cycle of the physical characteristic of the tissue.

In preferred embodiments, the triggering means further includes time delay means for triggering the spectrometer to produce the observation pulse after a predetermined time delay following the receipt of the sensing means output signal.

In another preferred embodiment for use with a tissue having a cyclical physical characteristic, the triggering means further includes multiple pluse means for triggering the spectrometer to produce a plurality of observation pulses within one cycle. Information is thus provided relating points in the cycle of the physical characteristic with changes in the concentration in the tissue of the chemical entity being measured.

One such entity for which such information is particularly valuable, as mentioned above, is phosphorous. The hydrogen atoms (protons) of important organic compounds may also exhibit changes in concentration and/or distribution corresponding to fluctuating physical characteristics of tissues. Still another entity of interest is sodium, which is known to differ in concentration in some tissues such as the heart, depending on the presence of certain disease states; it is likely that a comparison of cyclically fluctuating sodium levels will demonstrate even greater differences between healthy and diseased tissues. Additionally, any of the over 100 nuclei observable by NMR can be used with the present invention. Nuclei of particular biological interest are H-2, Li-6, Li-7, C-13, N-14, N-15, O-17, F-19, Na-23, Mg-25, P-31, Cl-35, Cl-37, K-39, K-41, Ca-43, Rb-85, Rb-87, AG-107, Ag-109, Cd-111, CD-113, Cs-133, Ba-135, BA-137, LA-139, Pt-195, Hg-199, Hg-201, Ti-203, and Ti-205.

The types of tissue in which the present invention can prove useful include the beating heart, skeletal muscle, smooth muscle-containing internal organs such as the peristaltic portions of the digestive tract, and tissues, e.g. the lungs, involved in breathing.

In practicing the invention, a fluctuating physical characteristic can be indicated in any suitable manner. For example, systole in the cardiac cycle can be indicated by a pressure wave, or by the QRS complex of the electrocardiogram.

In gating the NMR observation pulse trigger to a tissue, such as the heart, having a cylically fluctuating physical characteristic, it is desirable, in order to obtain a usefully large number of resolvable points, that the time resolution of the NMR observation be short compared to the length of time of a complete cycle; preferably the ratio is such that at least 4, and most preferably 50 or even 100 or more resolvable points exist. When necessary, greater time resolution can be provided by computer dissection of the free induction decay. The time resolution of Fourier-transformed NMR observations, although not always precisely definable, can usually be placed within limits, the lower limit being the duration of the NMR pulse used, and the upper limit being the intensity-weighted duration of the free induction decay.

When working with a tissue having a cyclically fluctuating physical characteristic, it is preferable that either the spin-lattice ($T_1$) relaxation times of all chemical species being measured remain unchanged throughout the cycle, or that all resonances be essentially unsaturated, or both. Satisfaction of one or both conditions insures that no artifacts are introduced into calculations of concentrations at various positions in the tissue cycle by NMR-related phenomena such as saturation. $T_1$ value constancy can be confirmed by determining $T_1$ values both randomly with respect to the cycle and gated to the cycle, and comparing the values.

It is also desirable to maintain the tissue preparation in a metabolically stable condition throughout each experiment, to be certain that observed concentration changes are not due to metabolic deterioration of the tissue. Metabolic stability throughout a cycle can be confirmed by taking the first and last spectra at the same position in the cycle, and superimposing them.

An additional control is desirable in a case where one chemical entity, e.g., phosphate, is being measured in two or more chemical species, e.g., ATP and CrP, in a tissue having a cyclically fluctuating physical characteristic such as the heart. At several points in the cycle, to insure that observed fluctuations are not a result of net loss or gain of the entity from the system, or of movement of the tissue from a more sensitive to a less sensitive area of the NMR probe during the cycle, the total amount of the entity is preferably summed at various points in the cycle to confirm constant concentration.

In the drawings,

FIG. 1 is a diagrammatic representation of perfusion apparatus associated with a beating heart;

FIG. 2 is a block diagram of NMR apparatus useful in practicing the invention;

Figure 5:
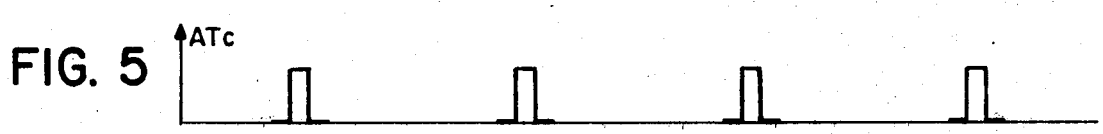
Figure 6:
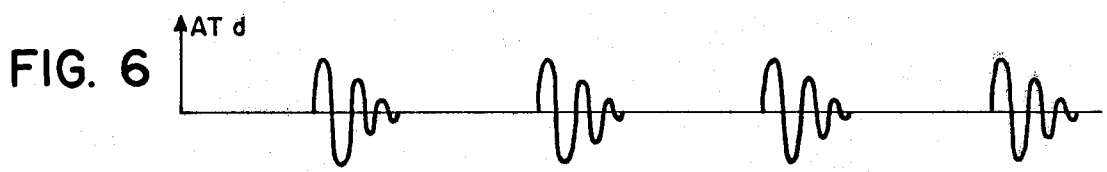
Figure 7:
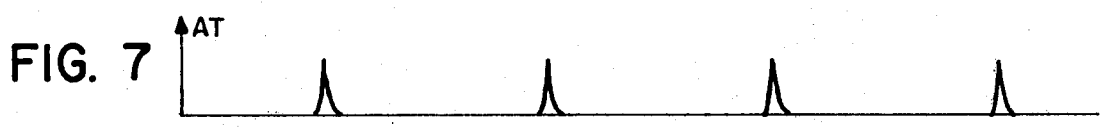
Figure 8:
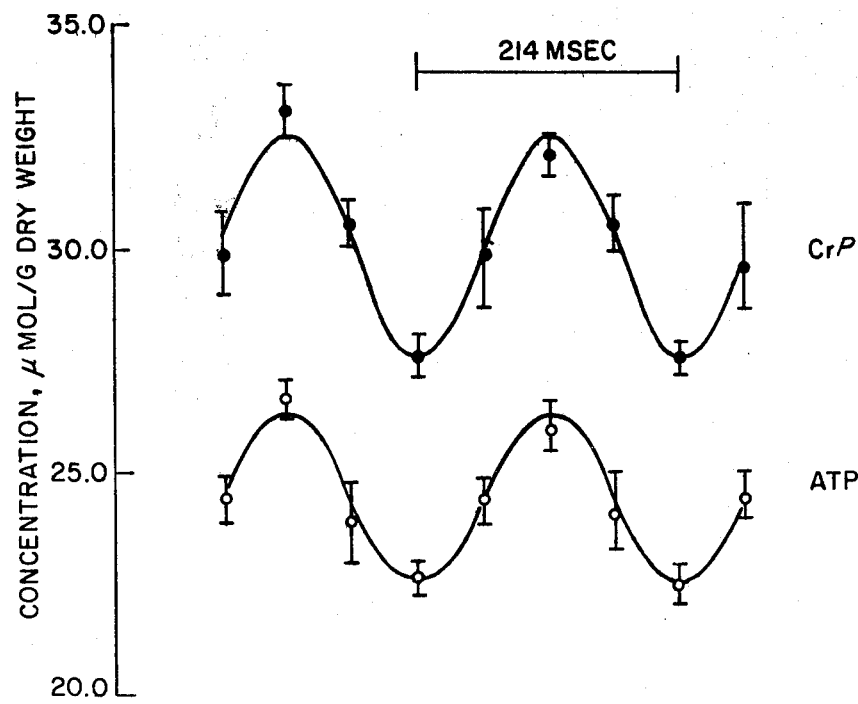

FIG. 5 is a timing diagram of the trigger pulses transmitted from pulse trigger 20 to spectrometer 22 of FIG. 1, FIG. 6 is a waveform diagram of the output of spectrometer 22 of FIG. 1;

FIG. 7 is a waveform diagram of the output of FIG. 6, Fourier-transformed to spectral form; and FIG. 8 is a graph of the relation between cardiac cycle and the concentration of high-energy phoshpate species.

The following specific example is intended to more particularly point out the invention, without acting as a limitation upon its scope.

EXAMPLE

This example is described in Fossel et al. (June, 1980) *Proc. Natl. Acad. Sci. USA* 77, 3654.

Referring to the FIGS. 1 and 2, a commercial Bruker Model HX-270 NMR spectrometer 22 was used, including a glass NMR tube 4 and a conventional Bruker $^{31}$P probe 19, schematically illustrated in FIGS. 1 and 2, and including a 63.5 kG magnet and radiofrequency coil, not specifically shown.

Heart 2 was obtained from a heparinized Sprague-Dawley rat which had been anesthetized with intraperitoneally-administered Nembutal (10 mg/100 g of body weight). To perform the excision, the rat's diaphragm was transected, incisions were made along both sides of the rib cage, and the anterior chest wall was folded back. The heart was excised and dropped into a beaker containing isotonic NaCl at 2° C.

The heart was then perfused and transferred to glass NMR tube 4, of outer diameter of 15 mm. All of the remaining apparatus shown in FIG. 1 was constructed of plastic. (A standard was run, for comparison purposes, using the same tube and NMR apparatus.) A cannula 6 was inserted through the aorta and the heart was washed out for 10 minutes, at 100 cm H$_2$O pressure with Krebs Henseleit bicarbonate buffer (pH 7.4) supplemented with 11 mM glucose. During the preliminary perfusion, the atria and aortic outflow 5 were clamped, and bypass 8 was open.

After the 10 minute washout, the left atrium 13 was cannulated and heart work was begun by unclamping this cannula 9 and aortic outflow 5 and clamping bypass 8. Variable-speed peristalitic pump 1 was adjusted to provide the desired left artial filling pressure or cardiac output, and the diameter of aortic outflow tube 5 was adjusted to achieve the desired aortic pressure. Pump 1 delivered 37° C. oxygenated buffer from gassing chamber 17, including gas inlet tube 11, through jacketed temperature control line 3 to the left atrium. Perfusate entering the atrium passed into the left ventricle, and ventricular contraction force fluid into the pressure chamber (*Windkessel*) 7, which contained air to provide pressure compliance. Pressure from ventricular contraction forced fluid through aortic outflow tube 5 to reservoir 10, 70–150 cm above the heart. Fluid was removed from NMR tube 4 by a vacuum tube (not shown) positioned below the heart. Cardiac work was controlled by varying the left ventricle filling pressure, or outflow resistance, or both.

Heart 2 was positioned in NMR tube 4 so that it was completely within probe 19. The heart's position in relation to probe 19 was determined by first determining the position of NMR tube 4 in relation to probe 19 and then calculating the % of the volume of NMR tube 4 occupied by the heart, by comparing the volume of the heart and the volume of the tube within the probe. The magnet generated a magnetic field around the heart of a field strength of 6.25 Tesla.

One end of hollow, saline-filled tubular pressure sensor 12 was sealed and connected to aortic outflow tube 5. The other end of sensor 12 was connected to Hewlett Packard Model 1280 pressure transducer 14, which in turn (referring to FIG. 2) was connected to Hewlett Packard Model 1064 C amplifier 16. Amplifier 16 was connected to digital pulse generator 18, which included a timing box, a one-shot multivibrator, and a Schmitt trigger.

Digital pulse generator 18 was connected to pulse trigger 20, which in turn was connected to NMR spectrometer 22, which included nucleus selector 24, and which was interfaced with a Nicolet BNC-12 computer 26 and a Diablo moving head disc 28.

Figure 3:
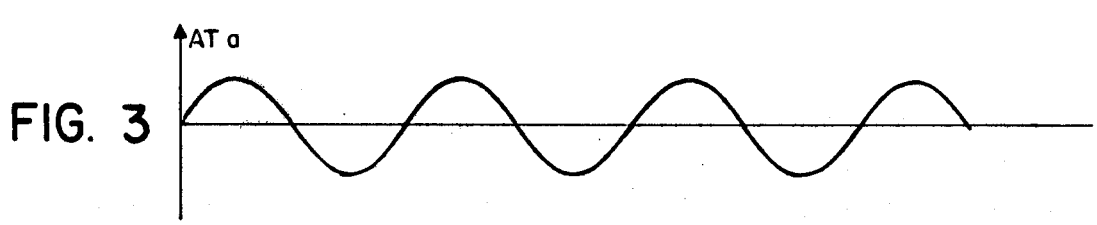
FIG. 3 is a waveform diagram of the fluctuating aortic pressure detected by transducer 14 of FIG. 2.

Pressure transducer 14 converted the fluctuating aortic pressure from the heart into the analog electrical signals shown diagrammatically in FIG. 3. These signals were amplified in amplifier 16, which also sensed the maximum pressure of each cardiac cycle. The amplified signals were then transmitted to digital pulse generator 18, which was programmable so that a time delay of any desired, predetermined length could be provided between the time of sensing of the maximum systolic heart beat and the triggering of the observation pulses, permitting a highly reproducible repetitive initiation of the NMR pulse at any position in the cardiac cycle. In the present example, observation pulses were gated to four points on the cardiac cycle: systole, diastole, mid-diastole, and mid-systole.

Figure 4:
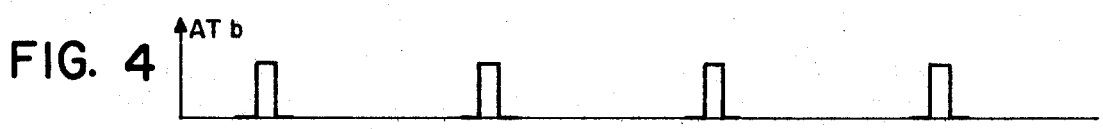
FIG. 4 is a digital pulse diagram corresponding to the waveform diagram of FIG. 3.

At each predetermined time interval following maximum cardiac pressure, digital pulse generator 18 transmitted a digital pulse to NMR pulse trigger 20; the digital pulses shown in FIG. 4 are shown transmitted at systole, i.e., after a time interval of essentially zero. NMR pulse trigger 20 then transmitted corresponding digital signals, shown in FIG. 5, to NMR spectrometer 22, which produced decaying sinusoidal observation pulses of about 109.3 MHz and 30° (12 μsec), as shown in FIG. 6. This radiofrequency was predetermined by nucleus selector 24, set to measure $^{31}$P in ATP and CrP molecules. The $^{31}$P in both species has a resonant frequency of about 109.3 MH$_2$ at a field strength of 6.25 T, the slightly different resonant frequency of each being the basis for distinguishing the two species. A $^{31}$P probe 19 of 15 mm outer diameter was used, and observation pulses were repeated at intervals which averaged 1.4 sec (±0.2 sec; the interval was slightly variable because of the dependence of pulse timing on the heart beat). The spectral output data from NMR spectrometer 22 are shown, Fourier transformed, in FIG. 7.

The free induction decay of the observation pulses was multiplied by an exponential in order to improve signal to noise ratios. This multiplication introduced a 25-Hz line broadening. Proton decoupling was not used; therefore, no nuclear Overhauser effect was present to complicate interpretation of resonance areas. Resonance areas were measured with a Hewlett Packard digital intergrator.

$T_1$ values were determined using the standard $180° - \pi - 90°$ inversion recovery pulse sequences. $T_1$ values were determined both randomly with respect to heart beat, and gated to the heart beat at both peak and minimum aortic pressures. Under the conditions of the experiment, for both the heart and the standard, at least 97% spin-lattice relaxation occurred, so that all resonances were essentially totally unsaturated.

Resonance assignments were made from comparison with authentic ATP and CrP samples, and quantitative results were obtained by comparison of experimental resonance areas with areas of resonances in spectra of the authentic samples of CrP, $P_i$, and ATP resulting from signal averaging under conditions comparable to those used in generating cardiac spectra.

NAD and NADH were unresolved from the ATP-$\alpha$ resonance, and their sum was estimated by subtracting the ATP-$\beta$ resonance area from the composite resonance containing ATP-$\alpha$, NAD, and NADH. No ADP (<2 $\mu$mol/g dry weight) was ever detected; i.e., the areas of the ATP-$\beta$ and $\gamma$ resonances were equal.

The average heart rate was 280 beats/min., giving an averge cardiac cycle of 214 msec. Because the upper limit of the Fourier-transformed NMR observation was 12 $\mu$sec (the length of the pulse), while the upper limit, at 63.5 KG, was less than 2 msec, there were potentially at least 100 resolvable points in the 214 msec cycle.

The first and last spectra taken on each heart were taken at the same position on the cycle, and superimposed. This confirmed that the heart remained metabolically stable throughout the experiment. The results of the above-described procedure are shown in FIG. 8, which shows that, in the beating heart, both ATP and CrP levels are inversely related to the phases of the aortic pressure wave.

Various modifications of the method and apparatus of the invention, within the spirit thereof and the scope of the appended claims, will occur to those skilled in the art.

What is claimed is:

1. Apparatus for dynamically measuring a chemical entity in living biological tissue having a physical characteristic capable of fluctuation, comprising
   an NMR pulse spectrometer capable of providing an observation pulse for instantaneously measuring the spectrum of said chemical entity in said biological tissue,
   sensing means for sensing said physical characteristic and providing an output signal, and
   triggering means responsive to said sensing means output signal and connected to said spectrometer for triggering said spectrometer to produce said observation pulse at a selected point in the course of said fluctuation of said physical characteristic of said tissue.

2. Apparatus for dynamically measuring a chemical entity in living biological tissue having a cyclical physical characteristic, comprising
   an NMR pulse spectrometer capable of providing an observation pulse for instantaneously measuring the spectrum of said chemical entity in said biological tissue,
   sensing means for sensing said cyclical physical characteristic and providing an output signal, and
   triggering means responsive to said sensing means output signal and connected to said spectrometer for triggering said spectrometer to produce said observation pulse at a selected point in the cycle of said physical characteristic of said tissue.

3. Apparatus as claimed in claim 1 or 2, wherein
   said triggering means further inlcudes time delay means for triggering said NMR pulse spectrometer to produce said observation pulse after a predetermined time delay following the receipt of said sensing means output signal.

4. Apparatus as claimed in claim 2, wherein
   said triggering means further includes multiple pulse means for triggering said NMR pulse spectrometer to produce a plurality of said observation pulses within said cycle of said physical characteristic of said tissue.

5. A method for dynamically measuring a chemical entity in living biological tissue having a physical characteristic capable of fluctuation, comprising
   sensing said physical characteristic, and
   providing an NMR pulse spectrometer observation pulse for instantaneously measuring the spectrum of said chemical entity in said biological tissue at a selected point in the course of said fluctuation, said pulse being provided in response to said sensing of said physical characteristic.

6. A method for dynamically measuring a chemical entity in living biological tissue having a cyclical physical characteristic, comprising
   sensing said cyclical physical characteristic, and
   providing an NMR pulse spectrometer observation pulse for instantaneously measuring the spectrum of said chemical entity in said biological tissue at a selected point in the cycle of said cyclical physical characteristic, said pulse being provided in response to said sensing of said physical characteristic.

7. A method as claimed in claim 5 or claim 6, further comprising the step of
   providing said observation pulse after a predetermined time delay.

8. A method as claimed in claim 6, further comprising the step of
   providing a plurality of said observation pulses within said cycle of said physical characteristic of said tissue.

9. A method as claimed in claim 6 or 8 wherein
   said tissue is a heart.

10. A method as claimed in claim 9 wherein
    said cyclical physical characteristic is change in blood pressure.

* * * * *

UNITED STATES PATENT AND TRADEMARK OFFICE
CERTIFICATE OF CORRECTION

PATENT NO. : 4,413,233
DATED : Nov. 1, 1983
INVENTOR(S) : Eric T. Fossel et al.

It is certified that error appears in the above-identified patent and that said Letters Patent is hereby corrected as shown below:

Column 1, insert before line 4:
--This invention was made with Government support in the form of NIH Grant Nos. P50-HL20552 and 1 R01-HL22542 and the Government has certain rights in the invention.--

Signed and Sealed this

Twenty-fifth Day of June 1985

[SEAL]

Attest:

DONALD J. QUIGG

*Attesting Officer*     *Acting Commissioner of Patents and Trademarks*